United States Patent [19]
Holt et al.

[11] Patent Number: 5,580,764
[45] Date of Patent: Dec. 3, 1996

[54] PROCESS FOR MICROBIAL REDUCTION PRODUCING 4(S)-HYDROXY-6(S)METHYL-THIENOPYRAN DERIVATIVES

[75] Inventors: Robert A. Holt, Yarm; Stuart R. Rigby, Eaglescliffe, both of United Kingdom

[73] Assignee: Zeneca Limited, London, England

[21] Appl. No.: 392,796

[22] PCT Filed: Aug. 20, 1993

[86] PCT No.: PCT/GB93/01776

§ 371 Date: Feb. 28, 1995

§ 102(e) Date: Feb. 28, 1995

[87] PCT Pub. No.: WO94/05802

PCT Pub. Date: Mar. 17, 1994

[30] Foreign Application Priority Data

Aug. 28, 1992 [GB] United Kingdom ............... 9218502
Feb. 25, 1993 [GB] United Kingdom ............... 9303824

[51] Int. Cl.⁶ .................... C12P 17/16; C12N 1/20; C12N 1/14
[52] U.S. Cl. ............. 435/118; 435/252.9; 435/255.4; 435/255.5; 435/256.1; 435/280
[58] Field of Search ................... 435/118, 280

[56] References Cited

U.S. PATENT DOCUMENTS 4,968,815  11/1990  Blacklock et al. .............. 549/66
5,039,802   8/1991  Blacklock et al. .............. 546/165
5,474,919  12/1995  Chartrain et al. ............... 435/118

FOREIGN PATENT DOCUMENTS 296879  12/1988  European Pat. Off. .

OTHER PUBLICATIONS

Jones, et al: "An asymmetric systhesis of MK–0417 Observationson oxazaborolidine–catalyzed reductions", Journal of Organic Chemistry, vol. 56, No. 2, Jan. 18, 1991, pp. 763–769.
Davies et al, J. Am. Chem Soc 101:5405–5410 (1979).
Jones J. B. Tetrahedron 42: 3351–3403 (1986).
Christen M. et al, J. Chem Soc., Chem Commun (1988) 264–266.

*Primary Examiner*—David M. Naff
*Assistant Examiner*—S. Saucier
*Attorney, Agent, or Firm*—Cushman Darby & Cushman, LLP

[57] ABSTRACT

A compound of formula

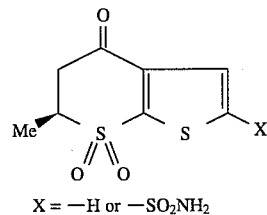

$X = -H$ or $-SO_2NH_2$ in which X is hydrogen or a group of formula $-SO_2NH_2$ is reduced to the trans (4S,6S) form of the corresponding alcohol by an enzyme reduction system.

10 Claims, No Drawings

PROCESS FOR MICROBIAL REDUCTION PRODUCING 4(S)-HYDROXY-6(S)METHYL-THIENOPYRAN DERIVATIVES

This invention relates to an asymmetric reduction process. The compound

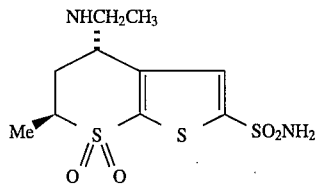
III is a topically active carbonic anhydrase inhibitor which is proposed for treatment of glaucoma. The compound with a methyl substituent in the 6 position in which the orientation is trans with regard to the 4-substituent (the 4S,6S diastereoisomer) is of therapeutic interest, but it is difficult to produce in the absence of a preponderant amount of the cis isomer (the 4R,6S diastereoisomer).

We have devised a process for producing a compound of formula

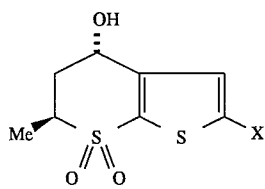
II in which X is hydrogen or a group of formula —$SONH_2$ which is a useful intermediate in the production of the desired trans (4S,6S) isomer III described above and derivatives thereof in an amount greater that that of the corresponding cis isomer from a compound of formula I

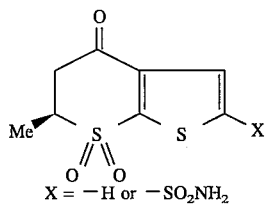
I

X = —H or —$SO_2NH_2$

Background chemistry related to the synthesis of these materials is disclosed in Jones, et al, J. Org. Chem 1991 56 763–769, Shinkai, J. Heterocyclic Chem. (1992) 29 627–639 and U.S. Pat. Nos. 4,968,814 and 4,968,815 and, in a publication made subsequently to the priority of this patent application, by Blacklock et al J. Org Chem. 1993 58 1672–1679.

The reduction of compound (I) using reducing agents such as boranetetrahydrofuran complex results in the formation of the (4R,6S) diastereoisomer (IV) as the major product (>90%) with the desired (4S,6S) trans diastereoisomer (II) accounting for a minor proportion of the product.

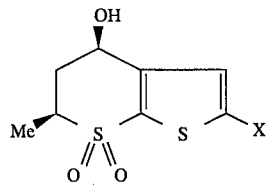
IV

Jones et al, J Org. Chem. (1991), 56, 763–769 have disclosed a method for the enantioselective reduction of a close analogue, compound (V), using bakers yeast (*Saccharomyces cerevisiae*). This reaction yields the (R)- and (S)-alcohols in the ratio 11:89.

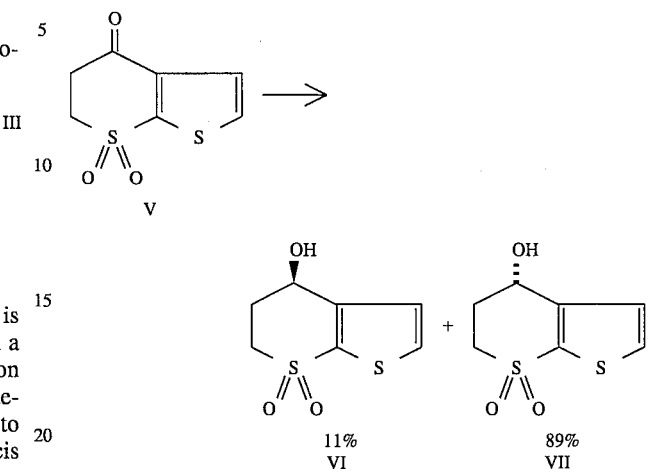

However, when a range of bakers' and brewers' yeasts were tested in the reduction of compound (I) the undesired cis diastereoisomer was the major product (60 to 85%). Examination of a wider range of microorganisms (bacteria, yeasts and fungi) demonstrated that most produced predominantly the undesired cis diastereoisomer. Surprisingly, however, we have found that it is in fact possible to produce the trans isomer in preponderant yield by enzyme reduction and have identified a range of microorganisms including bacteria, fungi and yeasts which are able to reduce compound (I) to the desired trans alcohol (II).

This invention comprises a process in which a compound of formula

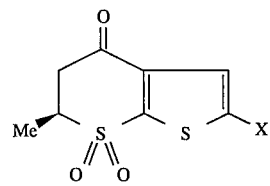

in which X is hydrogen or a group of formula —$SO_2NH_2$ is converted into a compound of formula

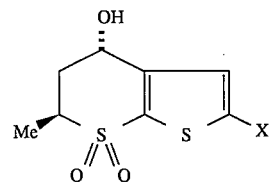

by contacting it with an enzyme reduction system. Suitable systems comprise a suitable oxido reductase enzyme and the reduced form of a co-factor for the enzyme. The enzyme reduction system may be provided as whole or broken cells of suitable microorganisms.

By "selectively" is meant that more of the trans (4S,6S) isomer is produced than of the cis (4R,6S) isomer. Preferably at least 60% and more preferably at least 80% for example at least 90% of the product is the trans isomer.

The process is preferably carried out at a pH of at most 8 and more preferably at most 6. We have found that the stereospecificity of the process is improved by operation under acidic conditions and it is preferred that it be carried out at a pH of 2 to 5. Microorganisms containing the enzyme reduction systems are surprisingly resistant to such conditions.

Suitable oxido reductases may be found by a process of screening. Examples of suitable reductases are those from *Lactobacillus plantarum* NCIMB 40027, *Pichia haplophila* CBS 2008, *Candida utilis* NCYC 322, *Lactobacillus buchneri* NCIMB 8818, *Aspergillus flavus oryzae* IMI 51983 or especially that from *Neurospora crassa* IMI 19419.

In general, bakers' and brewers' yeasts give the undesired cis product.

The co-factor may be for example, NADH, NADPH, FADH, FMNH and/or PQQ or any cofactor which occurs with the aforesaid enzyme in a microorganism. Preferably means to reduce the co-factor continuously are also present.

Very suitably the enzyme and co-factor may be supplied as broken or preferably whole cells of suitable microorganisms, and the cells may be supplied with a suitable substrate, for example a carbohydrate especially a sugar substrate, for example glucose, fructose or sucrose or glycerol or lactic acid. Such cells in general comprise means to reduce the co-factor by utilising the substrate.

The process is suitably carried out at temperatures of 20° C. to 40° C. preferably in aqueous media in which the pH may be pH2 to pH6 and preferably pH3 to pH5 and the concentrations of the reactant are suitably 5 g/liter to 10 g/liter. Substrate e.g. glucose is suitably present in concentrations of 5 g/liter to 50 g/liter and other nutrients for example yeast extract may be present.

EXAMPLE 1

Reduction of Ketone (I) (Where X=H) Using Tetrahydrofuranborane Complex.

To an oven dried 250 ml round bottom flask was added ketone (I) (500 mg) and the headspace flushed with dry nitrogen. To the flask was added 25 ml of anhydrous tetrahydrofuran and the resulting solution was stirred on ice to bring the temperature down to 5° C. Tetrahydrofuranborane complex (1.0 molar, 3 ml) was added dropwise during 15 minutes whilst maintaining the temperature at 5° C. After the final addition of tetrahydrofuran-borane complex the mixture was stirred for a further 30 minutes whilst allowing it to reach room temperature. Residual tetrahydrofuran-borane was quenched with methanol (25 ml), stirred for 30 minutes then a further 50 ml of methanol added. The product was recovered by removing the solvent under reduced pressure. The product was analysed by high pressure liquid chromatography (HPLC) using a Nova-Pak $C_{18}$ column (3.9 mm internal diameter×300 mm). Product and starting material were eluted using a solvent gradient consisting of 20 mM aqueous phosphoric acid and acetonitrile under the following conditions: time zero to 10 minutes aqueous phosphoric acid (20 mM), 92.5%: acetonitrile 7.5%; time 10 to 25 minutes the acetonitrile concentration was increased linearly to 27.5% whilst the aqueous phosphoric acid was decreased to 72.5%. The solvent flow rate was 1.0 ml/minute, The alcohols were eluted at 16 minutes (cis) and 17 minutes (trans) whilst the ketone was eluted at 24 minutes. Analysis performed on the sample obtained as described above indicated a yield of combined alcohols of 89% with a cis:trans ratio of 9:1,

EXAMPLE 2

Reduction of Ketone (I) (Where X=H) Using Whole Cells of the Bacterium *Lactobacillus plantarum*

Cells of *L. plantarum* NCIMB 40027 were grown in Oxoid MRS medium (obtained as a preformulated powder from Unipath Ltd., Basingstoke, England).

Eight two liter conical flasks each containing 1.5 liters of medium were inoculated with *L. plantarum* NCIMB 40027 and incubated at 28° C. for 24 hours on a rotary shaker. Cells were recovered by centrifugation and washed by resuspension in 100 mM sodium/potassium phosphate buffer pH 7.0.

Following recentrifugation the cells were resuspended in 500 ml of sodium/potassium phosphate buffer (100 mM, pH 7.0) to a concentration of 33 g/liter and added to a 1 liter conical flask. Ketone (I), 1.25 g, was dissolved in acetone, 2.5 ml, and added to the cell suspension along with 25 g of glucose. The mixture was incubated at 28° C. on a rotary shaker for 24 hours. Cells were removed by centrifugation and the supernatant extracted with 500 ml of dichloromethane. The aqueous phase was then saturated with sodium sulphate and re-extracted with 500 ml of dichloromethane. The combined dichloromethane extracts were dried with anhydrous magnesium sulphate and the solvent removed by rotary evaporation to yield a mixture of alcohol and residual ketone (I). The alcohol was purified by flash chromatography on a commercially available silica gel (Merck Kieselgel 60) (70–230 mesh ASTM) by elution with ethyl acetate: hexane (87.5:12.5 by volume) to yield 349 mg of trans alcohol (II) and 41 mg of cis alcohol (IV) as determined by the method of Example 1.

EXAMPLE 3

Reduction of Ketone (I) (Where X=H) Using Mycelium of the Fungus *Neurospora crassa*

*Neurospora crassa* IMI 19419 was grown in a mineral salts medium containing the following components (g/liter) glucose, 20; yeast extract, 2; dipotassium hydrogen phosphate, 1.9; sodium dihydrogen phosphate, 1.56; ammonium sulphate, 1.8; magnesium sulphate heptahydrate, 0.1; ferric chloride, 0.001; calcium carbonate. 0.002; zinc sulphate heptahydrate, 0.0001; manganese sulphate tetrahydrate, 0.0001. Two liter conical flasks containing one liter of medium were inoculated with spores of *Neurospora crassa* and incubated for 48 hours at 28° C. on an orbital shaker. The mycelium was recovered by filtration through a Whatman grade 113 filter paper and washed with water. Mycelium was resuspended to a concentration of 20 g dry weight/liter in 9.37 ml of sodium/potassium phosphate buffer (pH 7.0 or pH 8.0, 100 mM) and transferred to 15 ml screw cap vials. To the vials was added glucose (0.5 ml of a 50% solution) and a solution of ketone (I), 65 mg dissolved in acetone (0.13 ml). The vials were sealed and incubated with shaking at 28° C. for 21 hours. Analysis of the cell free supernatants by HPLC (as described in Example 1) indicated quantitative conversion of ketone to alcohol at both pH 7.0 and pH 8.0. At pH 7.0 the ratio of trans alcohol (III): cis alcohol (IV) was 94:6 whilst at pH 8.0 it was 89:11.

EXAMPLE 4

Reduction of Ketone (I) (Where X=H) Using Whole Cells of the Yeast *Pichia haplophila* CBS 2008

Cells of *Pichia haplophila* CBS 2008 were grown in the mineral salts, glucose, yeast extract medium described in Example 3. Two liter baffled conical flasks containing 400 ml of medium were inoculated with yeast and incubated for 48 hours at 28° C. on an orbital shaker. Cells were recovered from the culture by centrifugation and washed by resuspension in 100 mM citrate/phosphate buffer, pH 5.0. Cells were then resuspended to a final concentration of 6 g dry weight/liter in the citrate/phosphate buffer pH 5.0 and 10 ml dispensed into a 20 ml screw capped vial. To the vial was added glucose (0.2 ml of a 50% solution) and 14.5 mg of ketone (I) dissolved in 25 µl of acetone. The mixture was incubated at 28° C. for 22 hours on an orbital shaker, cells were removed by centrifugation and the supernatant analysed by HPLC as described in Example 1. The recovered supernatant contained no residual ketone, 0.65 mg cis alcohol (IV) and 12.13 mg of trans alcohol (III).

EXAMPLE 5

Example 4 was repeated using each of the microorganisms shown in the following table except that the cells were suspended in Na/K phosphate buffer (pH 7) (100 mM). The cell concentrations were 10–30 g dryweight/liter.

The conversions of the ketone fed and the percentage of trans isomer in the total reduced products are shown in Table 1.

TABLE 1

| Microorganism | Conversion % | Trans % |
|---|---|---|
| Neurospora crassa IMI 19419 | 100 | 95 |
| Lactobacillus plantarum NCIMB 40027 | 40 | 92 |
| Pichia haplophila CBS 2028 | 100 | 95 |
| Candida diddensiae ATCC 20213 | 31 | 52 |
| Candida utilis NCYC 322 | 33 | 81 |
| Pseudomonas oleovorans ATCC 29347 | 48 | 74 |
| Hansenula anomala CBS 2230 | 99 | 51 |
| Torulospora hansenii ATCC 20220 | 11 | 50 |
| Lactobacillus salivarius NCIMB 8818 | 96 | 69 |
| Lactobacillus buchneri NCIMB 8037 | 36 | 34 |
| Lactobacillus brevis NCIMB 1777 | 76 | 21 |
| Lactobacillus fermentum NCIMB 6991 | 84 | 54 |
| Aspergillus flavus oryzae IMI 51983 | 25 | 66 |
| Geotrichum candidum IMI 45619 | 99 | 15 |
| Arthrobacter petroleophagus ATCC 21494 | 99 | 42 |
| Candida lipolytica IFO 1437 | 95 | 35 |
| Pichia farinosa CBS 2007 | 13 | 45 |
| Pichia farinosa CBS 2006 | 12 | 51 |
| Pseudomonas putida NCIMB 9427 | 20 | 12 |
| Corynebacterium species ATCC 15529 | 99 | 27 |
| Corynebacterium paurometabolum ATCC 15530 | 97 | 20 |
| Pseudomonas aeruginosa ATCC 15525 | 80 | 17 |
| Beauveria bassiana ATCC 7159 | 46 | 21 |
| Beauveria bassiana NRRL 3352 | 41 | 53 |
| Proteus vulgaris NCIMB 67 | 24 | 13 |
| Xanthomonas campestris ATCC 13951 | 69 | 34 |
| Proteus mirabilis NCIMB 8268 | 26 | 13 |
| Beauveria brongniartii CBS 722.71 | 11 | 50 |
| Saccharomyces cerevisiae NCYC 240 | 21 | 15 |
| Candida oleophilia ATCC 20177 | 1 | 9 |
| Pichia pastoris BPCC 420 | 15 | 41 |
| Zygosaccharomyces rouxii NCYC 564 | 11 | 45 |
| Pichia capsulata CBS 837 | 99 | 10 |
| Geotrichum candidum IMI 96825 | 95 | 32 |
| Candida chalmersi NRRL Y 1260 | 37 | 42 |
| Pichia trehalophilia CBS 5361 | 98 | 36 |

EXAMPLE 6

Dependence on pH of Racemisation of Ketone (I) (Where X=H)

A 50% w/w solution of ketone (I) in acetone was made up (the enantiomeric excess of the (6S) ketone was 98.0%). Into separate vials was dispensed 2 ml of the following aqueous buffers (each supplemented with 50 mg of glucose to mimic biotransformation conditions)—sodium acetate (0.1M), pH 4.3; sodium citrate (0.1M), pH 5.0; potassium phosphate (0.1M), pH 6.5; sodium borate (0.05M); pH 9.0.

To the buffer solutions was added 10 mg of ketone I (as a solution in acetone), the vials were capped and maintained with shaking at 28° C. At intervals vials were extracted with ethyl acetate (1 ml twice), the organic layer separated, dried with anhydrous sodium sulphate and the ketone recovered by removal of solvent under a stream of dry nitrogen. The optical purity of the recovered ketone was determining by high pressure liquid chromatography (HPLC) using a Chiralcel O.D. column (0.46 mm internal diameter x 250 mm) with hexane:ethanol (9:1) as eluant, eluant flow rate 1 ml/minute and detection by UV absorbtion at 240 nm. The (R)-enantiomer eluted at 22.5 minutes whilst the (S)-enantiomer eluted at 24.2 minutes. Separate vials were extracted for each time point. The results are shown in Table 2.

TABLE 2 pH-DEPENDENCE OF RACEMISATION OF KETONE (I)

| | Enantiomeric Excess of (6S) - Ketone | | | |
|---|---|---|---|---|
| Time (Hours) | pH 4.3 | pH 5.0 | pH 6.5 | pH 9.0 |
| 1.5 | 97.6 | n.d. | 87.4 | n.d. |
| 2.5 | 97.2 | 98.0 | 82.8 | 65.8 |
| 3.5 | 97.0 | n.d. | 74.6 | n.d. |
| 4.5 | 97.8 | n.d. | 70.6 | n.d. |
| 5.5 | n.d. | 97.4 | n.d. | 37.6 |
| 22 | 97.4 | n.d. | 20.8 | n.d. |
| 23 | n.d. | 95.2 | n.d. | 9.8 | n.d. - not determined

EXAMPLE 7

Reduction of Ketone (I) (Where X=H) Using Mycelium of the Fungus *Neurospora crassa* Maintained at pH 4

*Neurospora crassa* IMI 19419 was grown in a Braun Biostat ED fermenter (15 liter working volume). The medium contained the following components (g/liter) glucose, 40; yeast extract, 2; magnesium sulphate heptahydrate, 1.2; dipotassium sulphate, 0.21; potassium dihydrogen phosphate, 0.69; phosphoric acid, 1.7; ferric chloride, 0.05; calcium carbonate, 0.07; zinc sulphate heptahydrate, 0.0035; manganese sulphate tetrahydrate, 0.0035; polypropylene glycol antifoam, 2. Ammonium hydroxide was used to bring the solution to pH 6.5 prior to inoculation. The fermenter was inoculated with 400 ml of culture previously grown for 24 hours using the medium and growth conditions described in Example 3. During fermentation the following parameters were controlled at the stated values, temperature 28° C.; pH, 6.5; air flow, 7.5 liters/minute; stirrer speed, 400 rpm. The culture was grown under these conditions for 30 hours at which point the mycelial concentration had reached 8.2 g dry weight/liter. At this point the temperature was increased to 34° C., the stirrer speed was automatically controlled to maintain a dissolved oxygen tension of 40% saturation and 2 molar hydrochloric acid was added to the fermenter to bring the culture to pH 4.0.

Ketone (I), 107 g, was dissolved in 300 ml of acetone. The acetone solution of ketone was added to the fermenter in small aliquots (15–30 ml) over a period of 13 hours. The rate of addition of ketone was adjusted such that the steady state concentration of ketone remained below 0.2 g/liter. This was monitored using the HPLC method described in Example 1.

When the ketone had been completely transformed the culture broth was removed from the fermenter and filtered through a Whatman 113 filter paper. The aqueous flitrate was extracted twice with 0.5 volume of ethyl acetate. The solvent was dried using anhydrous sodium sulphate and then removed by vacuum distillation to yield 90.9 g of alcohol.

The relative concentrations of the four disastereoisomers of the product alcohol were determined using two separate HPLC methods. The first method used a chiral stationary phase, Chiralcel O.D. (4.6 mm internal diameter×250 mm); eluant, hexane: ethanol (9:1); eluant flow rate, 1.0 ml/minute; detection by UV absorption at 250 min. The retention times were: (4S,6S) and (4R,6R) trans alcohols coeluted at 16.0 minutes; (4R,6S) cis alcohol, 16.8 minutes and (4S,6R) cis alcohol, 19.0 minutes.

In the second method derivatives were made by reacting the alcohols with (S)-α-methoxy-α-(trifluoromethyl) phenylacetyl chloride according to the method of Dale, Dull and Mosher, J. Org. Chem. 34, (9), 2543–2549 (1969). The derivatives were separated using a Zorbax silica column (4.6 mm internal diameter×250 mm); eluant, hexane: ethyl acetate (9:1); eluant flow rate, 2.0 ml/minute: detection by UV absorption at 260 nm. The retention times were: (4R 6R) trans alcohol, 20.1 minutes; (4S, 6S) trans alcohol and (4S, 6R) cis alcohol coeluted, 22.5 minutes; (4R, 6S) cis alcohol, 23.7 minutes.

The results of chromatographic analysis are shown in Table 3.

TABLE 3

| RATIO OF DIASTEREOISOMERS OF ALCOHOL (II) | |
|---|---|
| diastereoisomer | percentage of total alcohol |
| 1) Direct analysis on Chiralcel O.D. | |
| (4R, 6S) | 0.8% |
| (4S, 6R) | 0.3% |
| (4S, 6S) plus (4R, 6R) | 98.9% |
| 2) MTPA derivative analysis | |
| (4R, 6S) | 0.7% |
| (4R, 6R) | 0.1% |
| (4S, 6S) plus (4S, 6R) | 99.2% |

IMI—International Mycological Institute, Ferry Lane, Kew, Surrey United Kingdom TW9 30QR NCIMB—National Collection of Industrial and Marine Bacteria Ltd 23 St Machar Drive, Aberdeen United Kingdom AB2 1RY ATCC—American Type Culture Collection, 12301 Parklawn Drive Rockville, Maryland 20852 United States of America CBS—Centraal Bureau voor Schimmelcultures, Oosterstraat 1 3470 A G Baarn, Netherlands IFO—Institute for Fermentation, 17-85 Juso-honmachi 2-chome Yodogawa-ku, Osaka 532, Japan NRRL—Agricultural Research Service Culture Collection 1815 North University Street, Peoria, Ill. 61604 USA NCYC—National Collection of Yeast Cultures, The Food Research Institute, Colney Lane, Norwich, United Kingdom NR4 7UA

We claim:

1. A process which comprises converting a compound of formula:

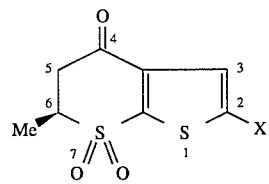

in which X is hydrogen or $SO_2NH_2$ into a compound of formula

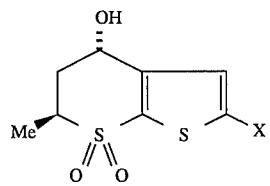

by contacting it with an intact microorganism or a broken cell preparation thereof, which produces more of the trans 4S, 6S isomer than of the cis 4R, 6S isomer and recovering the compound II.

2. The process as claimed in claim 1 in which at least 90% of the product is the 4S, 6S isomer.

3. The process as claimed in claim 1 in which the pH is 2 to 5.

4. The process of claim 1 wherein an intact microorganism is used and further comprising adding a substrate which permits the reduction of a cofactor by the microorganism.

5. The process as claimed in claim 4 in which the substrate is glucose, fructose, sucrose, glycerol or lactic acid.

6. The process as claimed in claim 1 in which the temperature is 20° C. to 40° C.

7. The process as claimed in claim 5 in which the concentration of glucose is 5 to 50 g/liter.

8. The process as claimed in claim 1 in which 5 to 10 g per liter of compound of formula I is present.

9. A process as claimed in claim 1 in which the microorganism is selected from the group consisting of *Lactobacillus plantarum, Pichia haplophila, Candida utilis, Lactobacillus buchneri* and *Aspergillus flavus oryzae*.

10. A process as claimed in claim 1 in which the microorganism is *Neurospora crassa*.

* * * * *